United States Patent
Nishiguchi et al.

(10) Patent No.: US 9,874,543 B2
(45) Date of Patent: Jan. 23, 2018

(54) ION MOBILITY ANALYZER AND MASS SPECTROMETER

(71) Applicant: SHIMADZU CORPORATION, Kyoto-shi, Kyoto (JP)

(72) Inventors: Masaru Nishiguchi, Hirakata (JP); Motohide Yasuno, Kyoto (JP); Ryo Fujita, Uji (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/108,918

(22) PCT Filed: Jan. 14, 2014

(86) PCT No.: PCT/JP2014/050406
§ 371 (c)(1),
(2) Date: Jun. 29, 2016

(87) PCT Pub. No.: WO2015/107612
PCT Pub. Date: Jul. 23, 2015

(65) Prior Publication Data
US 2016/0327516 A1 Nov. 10, 2016

(51) Int. Cl.
*G01N 27/62* (2006.01)
*H01J 49/42* (2006.01)
(Continued)

(52) U.S. Cl.
CPC .......... *G01N 27/622* (2013.01); *H01J 49/062* (2013.01); *H01J 49/004* (2013.01); *H01J 49/04* (2013.01); *H01J 49/4215* (2013.01)

(58) Field of Classification Search
CPC .. G01N 27/622; H01J 49/062; H01J 49/4215; H01J 49/004; H01J 49/04
(Continued)

(56) References Cited

U.S. PATENT DOCUMENTS

| 8,633,436 B2 | 1/2014 | Ugarov |
| 2011/0095175 A1* | 4/2011 | Bateman ............ G01N 27/624 250/282 |
| 2013/0161506 A1 | 6/2013 | Ugarov |

FOREIGN PATENT DOCUMENTS

| CN | 102954995 A | 3/2013 |
| CN | 103175888 A | 6/2013 |

(Continued)

OTHER PUBLICATIONS

Scott et al., "Noncontact measurement of electrostatic fields: Verification of modeled potentials within ion mobility spectrometer drift tube designs", 2007, Review of Scientific Intruments, 78, 035110.*
(Continued)

Primary Examiner — Nicole Ippolito
(74) Attorney, Agent, or Firm — Sughrue Mion, PLLC (57) ABSTRACT

A drift voltage generator applies voltages to a plurality of annular electrodes, respectively, so that a potential distribution $\varphi$ on an ion beam axis of an accelerating electric field created within a drift region satisfies $\partial^2\varphi/\partial Z^2 > 0$. Trailing ions undergo a higher rate of acceleration than preceding ions, so that a compressing force acts on an ion packet in the direction of the ion beam axis. Consequently, the ion packet is constantly confined to a smaller space in the direction of the ion beam axis, and ions having the same ion mobility form a narrower peak in a spectrum with the horizontal axis representing the drift time, so that the resolving power improves. A control unit switches the applied voltages so that a uniform accelerating electric field is created.

2 Claims, 6 Drawing Sheets (51) Int. Cl.
  *H01J 49/06* (2006.01)
  *H01J 49/00* (2006.01)
  *H01J 49/04* (2006.01)

(58) Field of Classification Search
  USPC .............................. 250/281, 282, 290, 291
  See application file for complete search history.

(56) References Cited

FOREIGN PATENT DOCUMENTS

| DE | 10 2012 220 552 A1 | 6/2013 |
| GB | 2500743 A | 10/2013 |
| JP | 2005-174619 A | 6/2005 |
| JP | 2013-134251 A | 7/2013 |

OTHER PUBLICATIONS

Written Opinion for PCT/JP2014/050406 dated Feb. 10, 2014. [PCT/ISA/237].
Jill R. Scott, J.R. et al., "Noncontact measurement of electrostatic fields: Verification of modeled potentials within ion mobility spectrometer drift tube designs", Review of Scientific Instruments, Mar. 23, 2007, 4 pages, vol. 78, Issue 3, Article 035110.
International Search Report of PCT/JP2014/050406 dated Feb. 10, 2014 [PCT/ISA/210].

\* cited by examiner

Fig. 5A CONVENTIONAL DEVICE

Fig. 5B PRESENT INVENTION

Fig. 6A
CONVENTIONAL DEVICE

Fig. 6B
PRESENT INVENTION

ION MOBILITY ANALYZER AND MASS SPECTROMETER

CROSS REFERENCE TO RELATED APPLICATIONS

This application is a National Stage of International Application No. PCT/JP2014/050406, filed Jan. 14, 2014, the contents of which are incorporated herein by reference in its entirety.

TECHNICAL FIELD

The present invention relates to an ion mobility analyzer as well as a mass spectrometer using an ion mobility analyzer.

BACKGROUND ART

Figure 8A:
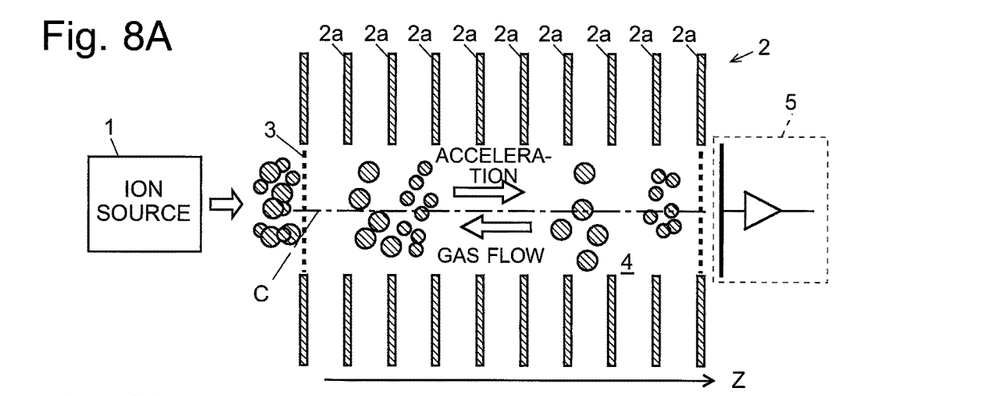
FIG. 8A is a schematic configuration diagram of a commonly used ion mobility analyzer.

When a molecular ion generated from a sample molecule is made to move in a gas medium (or liquid medium) under the effect of an electric field, the ion moves at a speed proportional to the mobility which is determined by the strength of the electric field, size of the molecule and other factors. Ion mobility spectrometry (IMS) is a measurement technique which utilizes this mobility for an analysis of sample molecules. FIG. 8A is a schematic configuration diagram of a commonly known ion mobility analyzer (for example, see Patent Literature 1).

Figure 8B:
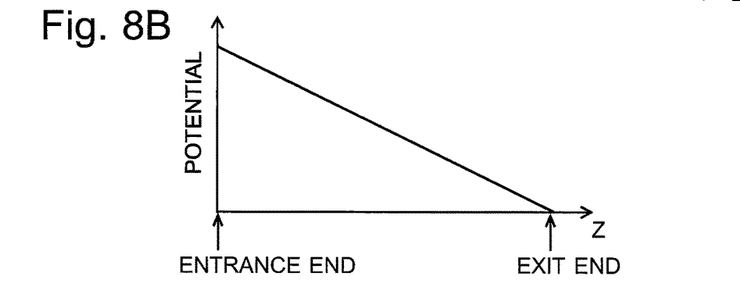
FIG. 8B is a schematic diagram showing the potential distribution on the ion beam axis within the drift region in the same analyzer.

This ion mobility analyzer includes an ion source 1 for ionizing component molecules in a sample, a drift region 4 for measuring the ion mobility provided within a housing (not shown) which, for example, has a cylindrical shape, and a detector 5 for detecting ions which have traveled through the drift region 4. A shutter gate 3 is provided at the entrance end of the drift region 4, in order to send the ions produced by the ion source 1 into the drift region 4 in a pulsed form confined to an extremely narrow width of time. The inside of the housing is maintained at an atmospheric pressure or a low-vacuum state of approximately 100 Pa. Within the drift region 4, a uniform electric field having a downward potential gradient in the moving direction of the ions (to accelerate the ions) is created by the DC voltages respectively applied to a large number of annular electrodes included in the drift electrode group 2 arrayed within the drift region 4. FIG. 8B is a schematic diagram showing the potential distribution on the ion beam axis C within the drift region 4. A stream of neutral diffusion gas is formed against the direction of the acceleration by this electric field.

The ions generated in the ion source 1 are temporarily stopped at the shutter gate 3 provided at the entrance end of the drift region 4. When the shutter gate 3 is opened in a pulse-like manner, the ions in the form of a packet are introduced into the drift region 4. The introduced ions travel along the downward potential gradient, colliding with the diffusion gas within the drift region 4. During this process, the ions are temporally separated according to the ion mobility which depends on the size, three-dimensional structure, charge and other properties of the ions. Consequently, ions having different ion mobilities reach the detector 5 with certain intervals of time. If the electric field within the drift region 4 is uniform, the collision cross-section between each ion and the diffusion gas can be estimated from the drift time required for that ion to pass through the drift region 4.

In Patent Literature 2, a method is proposed in which, instead of creating the uniform electric field within the drift region, the potential distribution on the ion beam axis is regulated so that the ions are focused in the radial direction of the ion path. In this case, although it is considerably difficult to estimate the collision cross-section between the ion and the diffusion gas, the loss of the ions due to the diffusion is reduced, so that a greater amount of ions can reach the detector. Consequently, a higher level of sensitivity can be achieved.

Figure 8C:
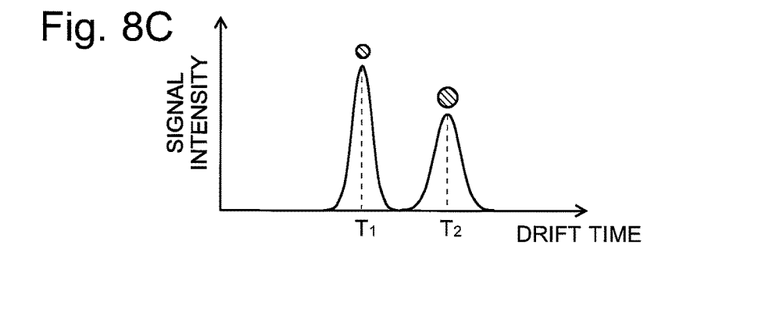
FIG. 8C is one example of the spectrum obtained with the same analyzer.

In general, the resolving power of an ion mobility analyzer is defined as [drift time]/[peak width] on a spectrum with the horizontal axis representing the drift time and the vertical axis representing the signal intensity, as shown in FIG. 8C. Accordingly, in order to improve the resolving power, it is necessary to devise a technique for increasing the drift time or decreasing the peak width. To increase the drift time, it is necessary to elongate the drift region. This approach is considerably restricted in terms of the size and cost of the device. Furthermore, due to the diffusion caused by the collision with the diffusion gas, the packet of ions becomes more dispersed as they fly a longer distance, so that the peak becomes broader as the drift time becomes longer. Therefore, even if the drift region is elongated in order to increase the drift time, there will be only a minor improvement in the performance because the peak width also simultaneously increases. In summary, elongating the drift region to improve the resolving power is not so beneficial because this method has the significant demerits of increasing the cost and size of the device while providing only a minor improvement in the performance.

CITATION LIST

Patent Literature

Patent Literature 1: JP 2005-174619 A
Patent Literature 2: CN 102954995 A

SUMMARY OF INVENTION

Technical Problem

The present invention has been developed to solve the previously described problem. Its objective is to provide an ion mobility analyzer which allows for an improvement in the resolving power and other performances of the device while reducing its size and cost, as well as a mass spectrometer using such an ion mobility analyzer.

Solution to Problem

The present invention developed for solving the previously described problem is an ion mobility analyzer for separating ions according to their ion mobilities by introducing the ions in a packet-like form into a drift region and making the ions fly in the drift region, the ion mobility analyzer including:

a) a plurality of annular or cylindrical electrodes arrayed along an ion beam axis for creating an accelerating electric field within the drift region; and b) a voltage supplier for applying voltages to the plurality of electrodes, respectively, with the voltages determined so that an electric field in which the downward gradient of the potential distribution on the central axis of the plurality of electrodes gradually becomes gentler in the moving direction of the ions is created at least within a portion of the accelerating electric field.

As noted earlier, in the conventionally and commonly used ion mobility analyzer, the voltages applied to the plurality of electrodes are set so that the axial potential distribution on the ion beam axis in the moving direction of the ions has a downward linear gradient. Therefore, the accelerating electric field becomes a uniform electric field.

By comparison, in the ion mobility analyzer according to the present invention, the voltages applied to the electrodes are set so that the axial potential distribution φ satisfies $\partial^2\varphi/\partial Z^2 > 0$ at least within a portion of the accelerating electric field. This is an axial potential distribution in which the downward gradient gradually becomes gentler. An accelerating electric field having such a potential distribution affects the motion of the ions as follows: If the ions, which are initially clustered (in the form of a packet) at the point of introduction into the drift region, are spread along the ion beam axis as they move forward, the trailing ions in the spread cluster undergo a higher rate of acceleration than the preceding ions. Such a force which acts on the ions due to the acceleration is a force which compresses ions having the same ion mobility into a smaller space along the ion beam axis and thereby reduces the variation in the drift time of the ions having the same ion mobility. Consequently, for example, the peak observed on the spectrum with the horizontal axis representing the drift time will be narrower than in the case where the accelerating electric field is a uniform electric field, so that the resolving power improves.

As is commonly known, the spatial potential distribution in an electric field can be formulated by Laplace's equation. According to the formulation of Laplace's equation for an axially symmetrical coordinate system, an ion placed within an electric field having an axial potential distribution expressed as $\partial^2\varphi/\partial Z^2 > 0$ experiences a force which pulls the ion radially outward. Therefore, when ions pass through such an electric field, the trajectories of the ions radially diverge. Some of the ions come into contact with the electrodes and disappear, while some other ions miss the ion-receiving region at the exit end of the drift region. Consequently, the sensitivity may possibly become lower. In the device described in Patent Literature 2, this problem is addressed by regulating the applied voltages so as to create an axial potential distribution expressed as $\partial^2\varphi/\partial Z^2 < 0$ and thereby induce a force which pushes the ions radially inward so that the ions are focused into a region near the ion beam axis.

As already noted, an axial potential distribution which satisfies $\partial^2\varphi/\partial Z^2 > 0$ promotes the spreading of the ions in the radial direction and therefore is less favorable than the uniform accelerating electric field in terms of the measurement sensitivity.

Accordingly, in the ion mobility analyzer according to the present invention, it is preferable to further provide:

a controller for controlling the voltage supplier in such a manner that the voltages respectively applied to the plurality of electrodes are changed so as to regulate the effect of compressing the ions into a smaller space in the accelerating direction within the accelerating electric field.

More preferably, the ion mobility analyzer according to the present invention may be configured so that the measurement mode is switchable between a high-resolution measurement mode for giving priority to the resolving power and a high-sensitivity measurement mode for giving priority to sensitivity, and the controller sets the voltages applied to the plurality of electrodes, respectively, so that the electric field in which the downward gradient of the potential distribution on the central axis of the plurality of electrodes gradually becomes gentler in the moving direction of the ions is created in at least a portion of the accelerating electric field when the high-resolution measurement mode is specified, while the controller sets the voltages applied to the plurality of electrodes, respectively, so that an electric field in which the potential distribution has a uniform potential gradient is created when the high-sensitivity measurement mode is specified.

In this configuration, when the high-resolution measurement mode is specified, the ion packet is compressed in the accelerating direction in the previously described manner at least within a portion of the accelerating electric field. Therefore, the ions having the same ion mobility become less spread in the accelerating direction, so that a high level of resolving power is achieved. On the other hand, when the high-sensitivity measurement mode is specified, a uniform accelerating electric field is created within the drift region, as in the conventional case. In this mode, although the resolving power is lower than in the high-resolution measurement mode, the spread of the ions in the radial direction is suppressed, so that the loss of the ions is reduced and a higher level of analysis sensitivity is achieved than in the high-resolution measurement mode. Since the measurement can be switched in this manner between the specifically sensitivity-oriented mode and the specifically resolution-oriented mode, a result which correctly matches the purpose of the analysis can be obtained.

Furthermore, in this configuration, the operation can be quickly switched between the high-sensitivity measurement mode and the high-resolution measurement under the command of the controller. Therefore, for example, within a comparatively short period of time in which a specific component isolated by a liquid chromatograph is being introduced, the measurement can be switched between the high-sensitivity mode and the high-resolution mode to obtain measured results in both modes.

As with the conventionally known ion mobility mass spectrometer, the ion mobility analyzer according to the present invention can be applied in a mass spectrometer which detects ions after separating them according to their mass-to-charge ratios.

In other words, the mass spectrometer according to the present invention is characterized in that the previously described ion mobility analyzer according to the present invention is placed between an ion source for producing ions originating from a sample and a mass separator for separating ions according to their mass-to-charge ratios, and the ions separated according to their ion mobilities in the ion mobility analyzer are further separated by the mass separator before being detected.

The mass spectrometer according to the present invention is capable of detecting an ion having a specific mass-to-charge ratio and a specific ion mobility with a high level of resolving power.

Advantageous Effects of the Invention

In the ion mobility analyzer and the mass spectrometer according to the present invention, the resolving power is improved by merely changing the voltages applied to the electrodes for the acceleration, without elongating the drift region. Accordingly, a high level of performance can be achieved while avoiding the increase in the cost and size of the device.

DESCRIPTION OF EMBODIMENTS

One embodiment of the ion mobility analyzer according to the present invention is hereinafter described with reference to the attached drawings.

Figure 1:
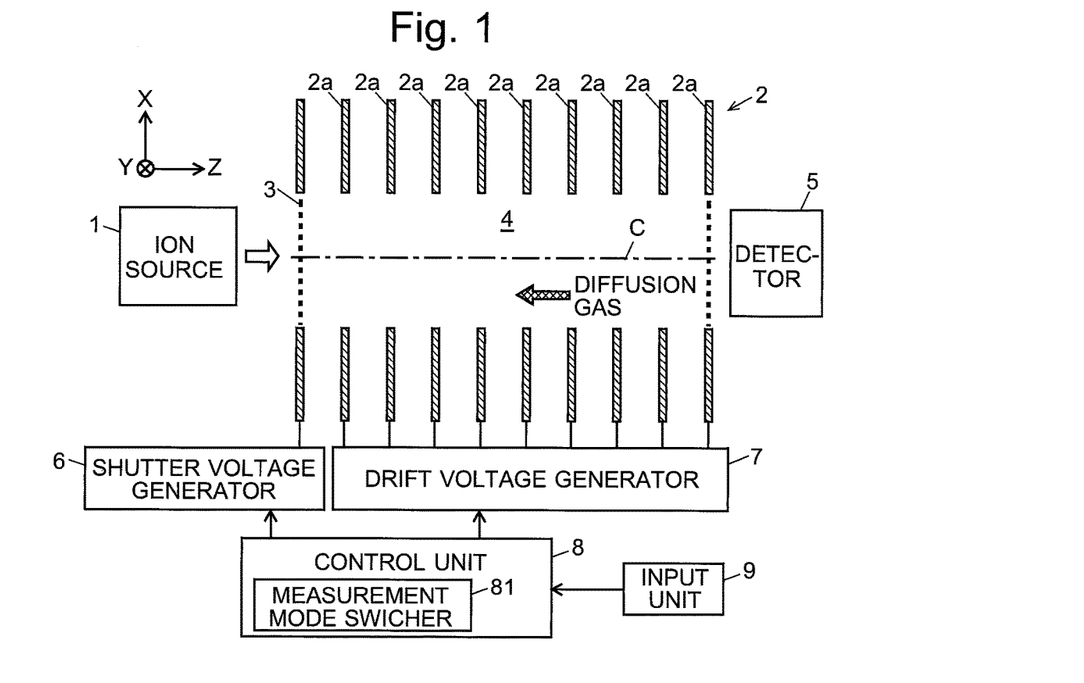
FIG. 1 is a schematic configuration diagram of an ion mobility analyzer as one embodiment of the present invention.

FIG. 1 is a schematic sectional view of the ion mobility analyzer of the present embodiment. The components which are identical or correspond to the counterparts in the ion mobility analyzer already described with reference to FIG. 8A are denoted by the same numerals.

As shown in FIG. 1, some components of the conventional ion mobility analyzer are identical to those used in the ion mobility analyzer of the present embodiment, such as the shutter gate 3 placed at the entrance end of the drift region 4, the drift electrode group 2 including a plurality of annular or cylindrical electrodes 2a arrayed in the drift region 4, and the detector 5 placed behind the exit end of the drift region 4. The electrodes 2a in the drift electrode group 2 are individually supplied with a predetermined level of voltage from a drift voltage generator 7. The shutter gate 3 is supplied with a pulsed voltage at a predetermined timing from a shutter voltage generator 6. The control unit 8, which includes a measurement mode switcher 81 as its functional block, controls each of the voltage generators 6 and 7. The control unit 8 has an input unit 9 connected to it. Using this input unit 9, users can perform operations, such as specifying the measurement mode.

The major difference between the ion mobility analyzer of the present invention and the conventional device exists in the voltages applied from the drift voltage generator 7 to the electrodes 2a in the process of separating ions according to their ion mobilities. In the device of the present embodiment, the potential distribution on the central axis of the drift electrode group 2, i.e. on the ion beam axis C, is appropriately adjusted so as to compress an ion packet in its travelling direction and thereby improve the resolving power.

In general, within the working pressure range of the drift region in the ion mobility analyzer, ions are cooled to the temperature of the diffusion gas due to the collision with this gas while they fly a distance not longer than 1 mm. If the inside of the housing is at room temperature, the amount of energy of a cooled ion is on the order of 0.01 eV, which is negligible as compared to the amount of energy imparted from the electric field. Therefore, as is commonly known, the macroscopic drift speed v of the ion is given by v=KE, where K is the ion mobility specific to the ion species and E is the strength of the electric field. Now, consider the case where an ion packet travelling along the ion beam axis C within the drift region 4 has center position $z_0$ and width $\Delta z$ in the axial direction (i.e. in the Z-axis direction) at time $t_0$.

If the diffusion is not considered, the size $\Delta z'$ of the ion packet as measured after a slight amount of time $\Delta t$ from $t_0$ is given by the following equation (1):

$$\Delta z' = \Delta z + K\{E(z_0+\Delta z/2) - E(z_0-\Delta z/2)\}\Delta t \qquad (1)$$

On the assumption that $\Delta z$ is extremely small, the second order approximation of $\Delta z'$ gives the following equation (2):

$$\Delta z' = \Delta z\{1 - K(\partial^2 \varphi / \partial z^2)\Delta t\} \qquad (2)$$

where $E = -\nabla \varphi$ has been used. This equation shows that $\Delta z' < \Delta z$ within a range where $\partial^2 \varphi / \partial z^2 > 0$, which means that the ion packet is compressed in the travelling direction due to the electric field. In other words, by adjusting the axial potential distribution so that it satisfies $\partial^2 \varphi / \partial z^2 > 0$ and does not form a linear gradient (i.e. $\partial^2 \varphi / \partial z^2 = 0$) as in the conventional device, it is possible to compress the ion packet in the travelling direction and thereby achieve a higher level of resolving power. The axial potential distribution can be appropriately adjusted by changing the values of the voltages applied to the electrodes 2a.

Figure 2:
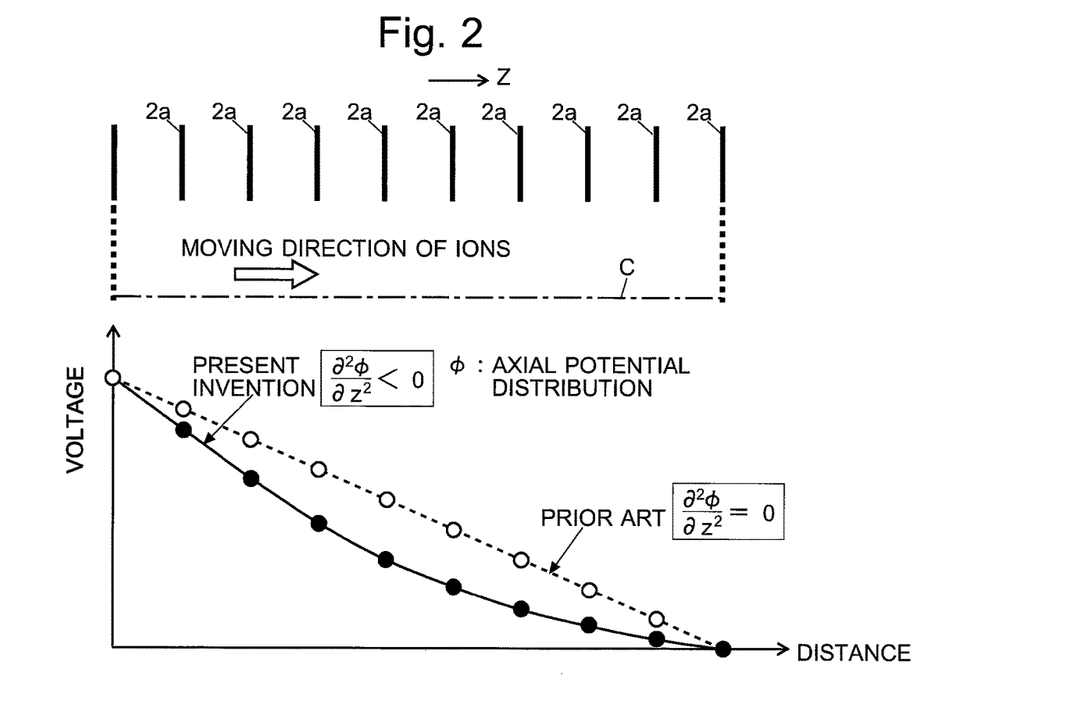
FIG. 2 is a schematic diagram showing the axial potential distribution within the drift region in the ion mobility analyzer of the present embodiment.

FIG. 2 schematically shows a comparison between the ion mobility analyzer of the present embodiment and the conventional device in terms of the voltages respectively applied to the electrodes 2a. It should be noted that this example is concerned with the case where the target of the analysis is a positive ion.

As shown in FIG. 2, in the conventional case, a plurality of voltages which form a downward linear gradient in the accelerating direction (i.e. the Z-axis direction) are applied to the equally spaced electrodes 2a. The axial potential distribution of the accelerating electric field created by such accelerating voltages also has a downward linear gradient in the accelerating direction. In other words, in principle, the axial potential distribution $\varphi$ satisfies $\partial^2 \varphi / \partial Z^2 = 0$, and the accelerating electric field is a uniform electric field with no change in the rate of acceleration. By comparison, in the ion mobility analyzer of the present embodiment, a plurality of voltages forming a downward gradient which gradually become gentler in the accelerating direction are applied to the equally spaced electrodes 2a. Therefore, the axial potential distribution $\varphi$ of the accelerating electric field satisfies $\partial^2 \varphi / \partial Z^2 > 0$ over the entire drift region 4.

It is commonly known that the behavior of an ion in a static accelerating electric field is subject to the constraints based on Laplace's equation. According to this theory, an accelerating electric field having an axial potential distribution which satisfies $\partial^2 \varphi / \partial Z^2 > 0$ has the effect of expanding the ion packet in the radial direction (in the directions orthogonal to the ion beam axis C). Consequently, while being compressed in the travelling direction, the ion packet is also unfavorably spread in the radial direction. If the packet is excessively spread, the ions may possibly come in contact with the electrodes and disappear, or they may possibly miss the ion detection surface of the detector 5 and be wasted. Accordingly, the ion mobility analyzer of the present embodiment is configured so as to create a uniform accelerating electric field as in the conventional device and disable the function of compressing the ion packet in the travelling direction of the ions when the measurement sensitivity is critical while the resolving power is not considered to be so important. This point will be described in detail later.

Figure 3A:
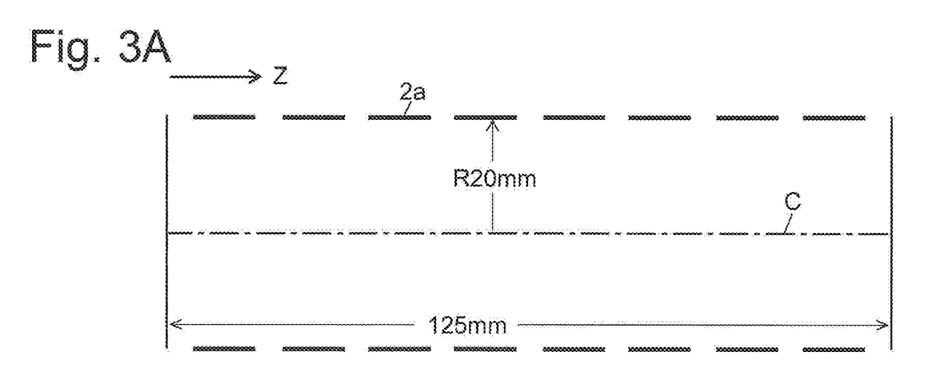
FIGS. 3A and 3B show an electrode model for the simulation of an ion trajectory in the ion mobility analyzer of the present embodiment.
Figure 3B:
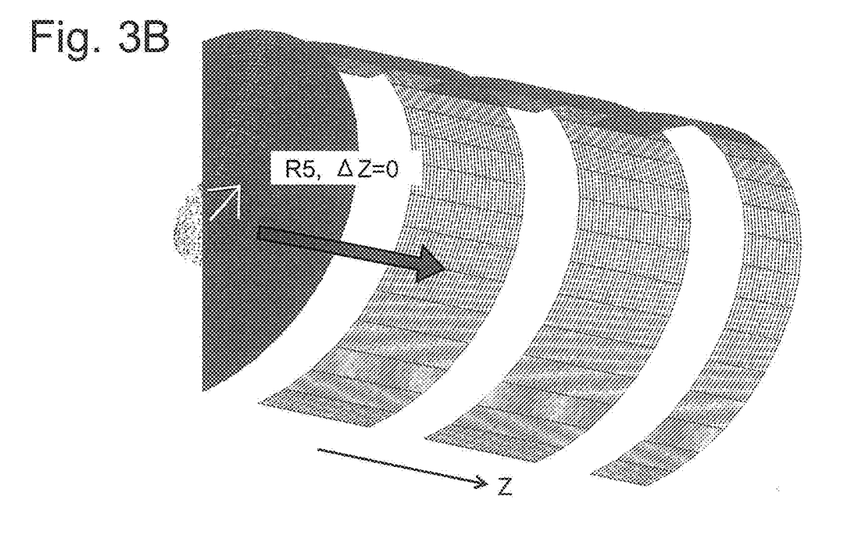
Figure 4:
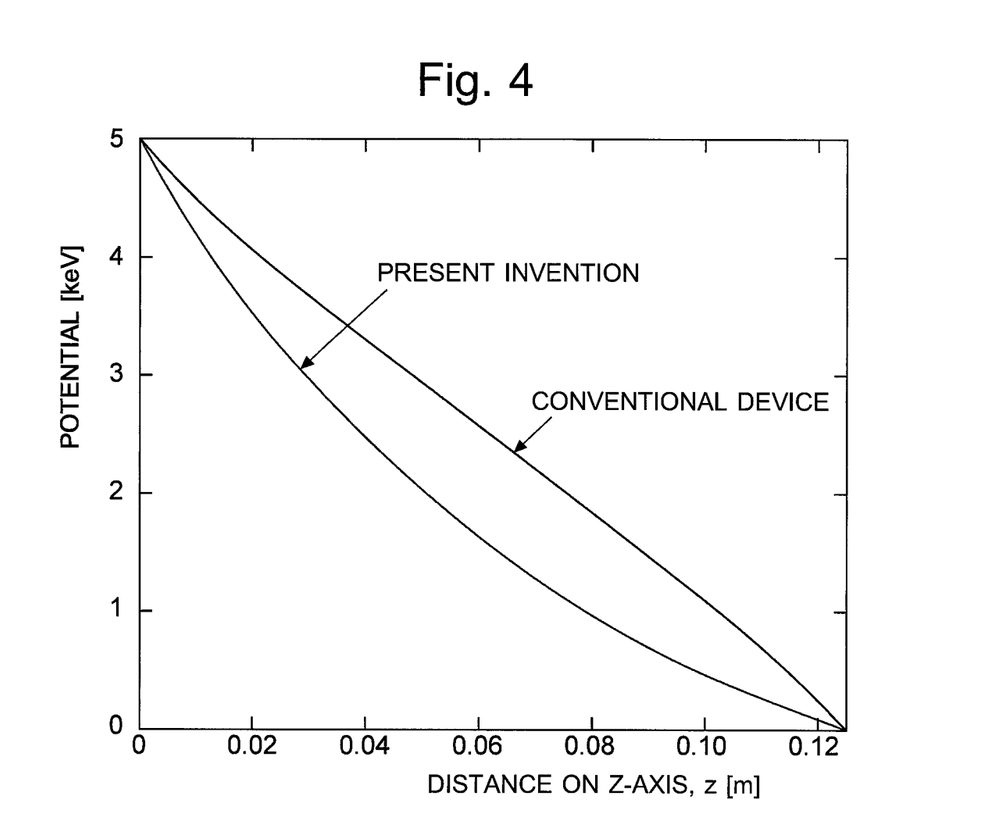
FIG. 4 shows the axial potential distribution assumed in the simulation calculation of the ion trajectory in the ion mobility analyzer of the present embodiment.
Figure 5A:
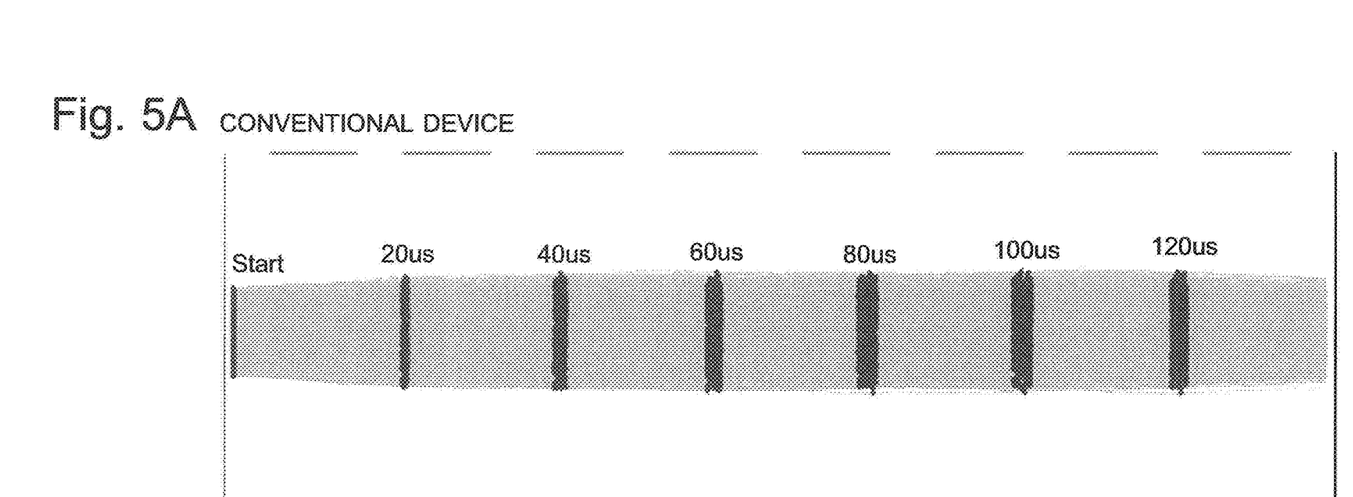
FIGS. 5A and 5B show the result of the simulation of the ion trajectory in the ion mobility analyzer of the present embodiment.
Figure 5B:
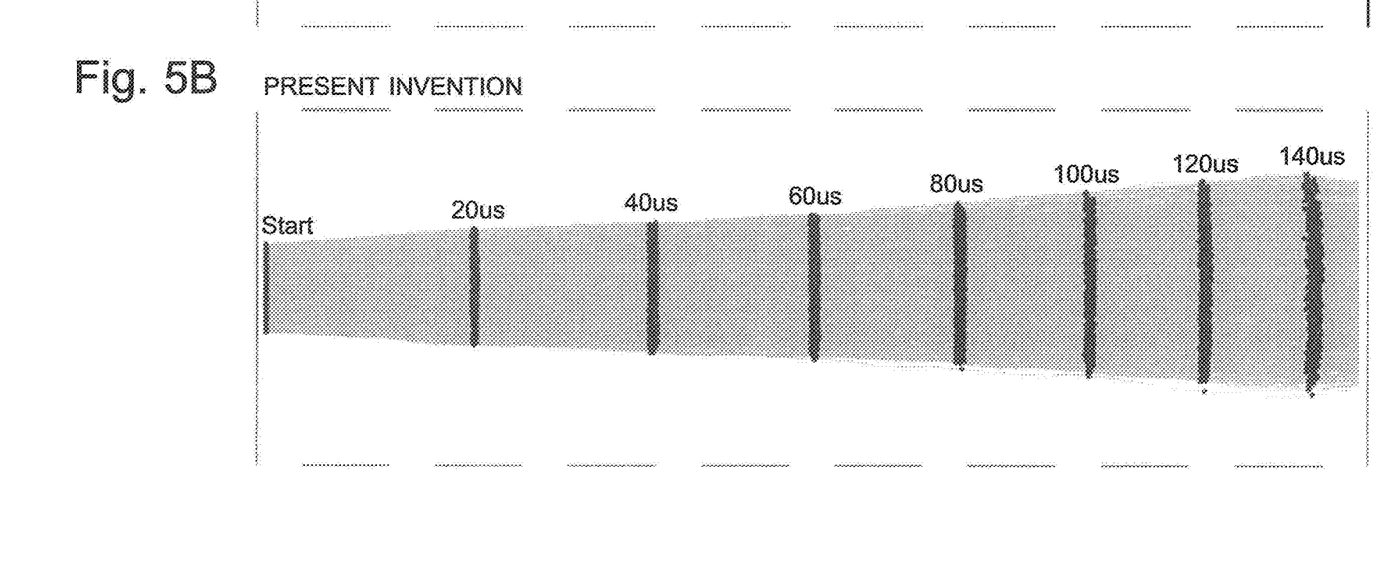

Hereinafter described is an ion trajectory simulation which was performed to confirm the previously described ion-packet compression effect. FIGS. 3A and 3B show the electrode model used for the simulation of the ion trajectory, and FIG. 4 shows the axial potential distribution in the ion mobility analyzer of the present embodiment and a conventional device. FIG. 5A shows the result of the simulation of the ion trajectory in the ion mobility analyzer of the present embodiment, while FIG. 5B shows the result of the simulation of the ion trajectory in the conventional device. It should be noted that the flow of the diffusion gas was not assumed in the simulation calculation; only the collision with the diffusion gas was considered.

As shown in FIG. 3A, in the simulation calculation, the electrode group was assumed to be an array of eight cylindrical electrodes $2a$ with an entire length of 0.125 m in the Z-axis direction and a radius of 0.02 m. As the initial conditions, the ion packet was assumed to have an initial width (spread) of zero in the travelling direction and be distributed in the form of a circular disc with a radius of 5 mm at the entrance end of the drift region 4. Simulating the motion of the ions under atmospheric pressure would require an excessively long computation time due to their frequent collision with the diffusion gas. Therefore, the pressure within the drift region 4 was assumed to be at 1000 Pa. Under this pressure, the mean free path of the ions is approximately 6 μm.

If eight levels of voltage 4049.4 V, 3197.5 V, 2444.4 V, 1790.1 V, 1234.6 V, 777.8 V, 419.8 V and 160.5 V are respectively applied to the eight electrodes $2a$ along the travelling direction of the ions, the axial potential distribution will satisfy $\partial^2\varphi/\partial Z^2 > 0$ over almost the entire length of the drift region 4, as shown in FIG. 4. By comparison, if eight levels of voltage 4444.4 V, 3888.9 V, 3333.3 V, 2777.8 V, 2222.2 V, 1666.7 V, 1111.1 V and 555.6 V are respectively applied to the eight electrodes $2a$ along the travelling direction of the ions, the axial potential distribution will satisfy $\partial^2\varphi/\partial Z^2 = 0$ over almost the entire length of the drift region 4.

Figure 6A:
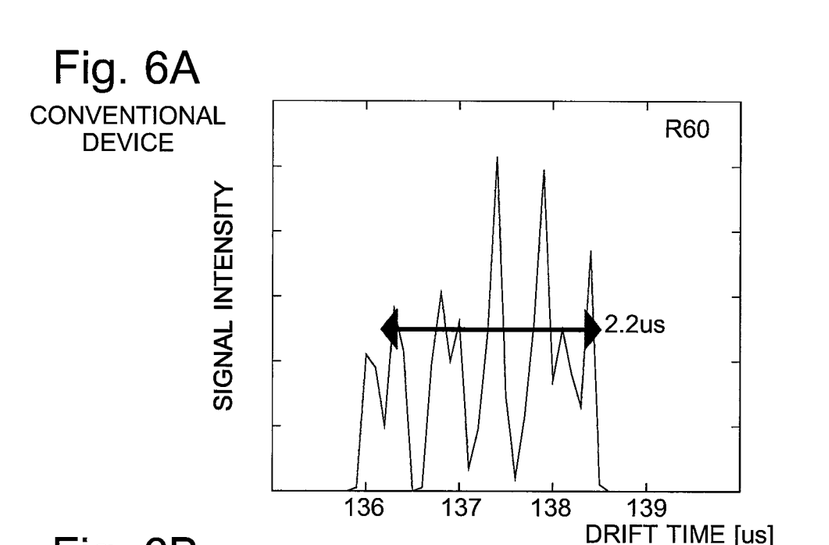
FIGS. 6A and 6B show the spectrum calculated by the simulation of the ion trajectory in the ion mobility analyzer of the present embodiment.
Figure 6B:
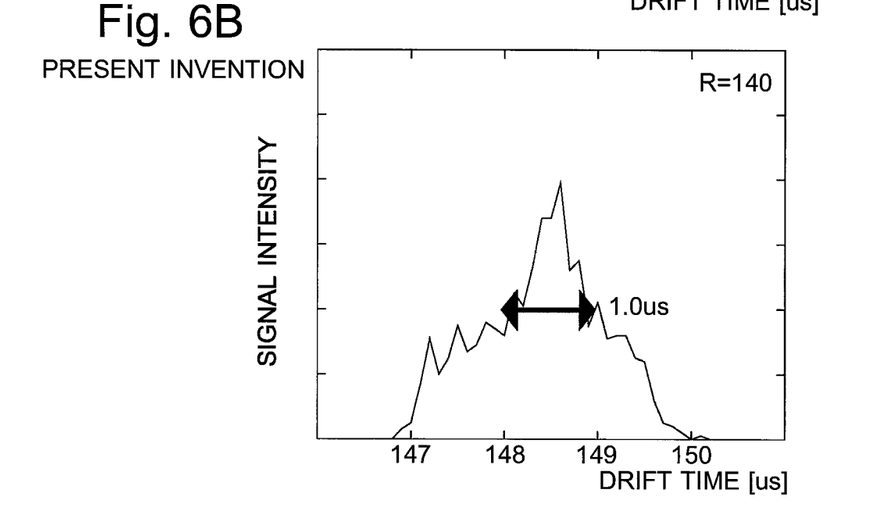

As shown in FIG. 5A, when the ions move in the uniform accelerating electric field in the conventional device, the ion packet becomes increasingly spread in the travelling direction of the ions due to the diffusion. By comparison, in the device of the present embodiment, as shown in FIG. 5B, the ion packet moving forward is compressed in its travelling direction, so that the ion packet is constantly confined within a small space in the traveling direction. The widths of the drift-time peaks on the spectra shown in FIGS. 6A and 6B demonstrate that the device of the present embodiment has a higher level of resolving power than the conventional device.

However, as is evident from FIG. 5B, in the device of the present embodiment, the ion trajectory gradually diverges in the radial direction. This is disadvantageous in terms of the sensitivity. From this simulation result, it is understandable that the switching of the mode between the high-resolution measurement mode and high-sensitivity measurement mode by the change in the voltages applied to the electrodes $2a$ is beneficial.

By performing the previously described simulation calculation or an experiment using a real device (or otherwise), it is possible to determine appropriate voltage values for achieving a high level of resolving power while maintaining a sufficient level of sensitivity. Accordingly, in the ion mobility analyzer of the present embodiment, information about the voltage values for each of the high-resolution and high-sensitivity measurement modes is stored in a memory provided in the control unit 8 (or a similar storage). In an actual analysis, for example, when a user operating the input unit 9 specifies either the high-resolution measurement mode or the high-sensitivity measurement mode and commands the device to perform the analysis, the measurement mode switcher 81 reads the voltage-value information for the specified measurement mode from the memory and controls the drift voltage generator 7 based on that voltage-value information. The drift voltage generator 7 applies the predetermined voltages to the respective electrodes $2a$ in the drift electrode group 2, whereby either an accelerating electric field with the rate of acceleration gradually decreased in the travelling direction of the ions, or a uniform accelerating electric field is created within the drift region 4. In this manner, the ion mobility analyzer according to the present embodiment can perform the measurement with importance placed on either the resolving power or sensitivity according to the purpose of the analysis (or other factors).

The degree of compression of the ion packet in the travelling direction as well as its amount of spread in the radial direction change depending on the axial potential distribution within the drift region 4. Therefore, the device may also be configured so that the applied voltages can be adjusted for a fine tuning of the axial potential distribution according to the purpose of the analysis (or other factors) in addition to the previously described switching of the two measurement modes.

It is also possible to configure the device so that the electric field with the axial potential distribution $\varphi$ satisfying $\partial^2\varphi/\partial Z^2 > 0$ is created at least in a portion of the drift region 4 along the ion beam axis C but not the entire drift region 4, while a uniform electric field with the axial potential distribution $\varphi$ satisfying $\partial^2\varphi/\partial Z^2 = 0$ is created in the other portions. In this manner, the device performance can be tuned so as to achieve the desired specifications (resolving power and sensitivity) over the entire drift region 4. Accordingly, a device which achieves the desired specifications can be more flexibly designed than the conventional one. The improved degree of freedom of the device design also leads to a reduction of the device cost.

Figure 7:
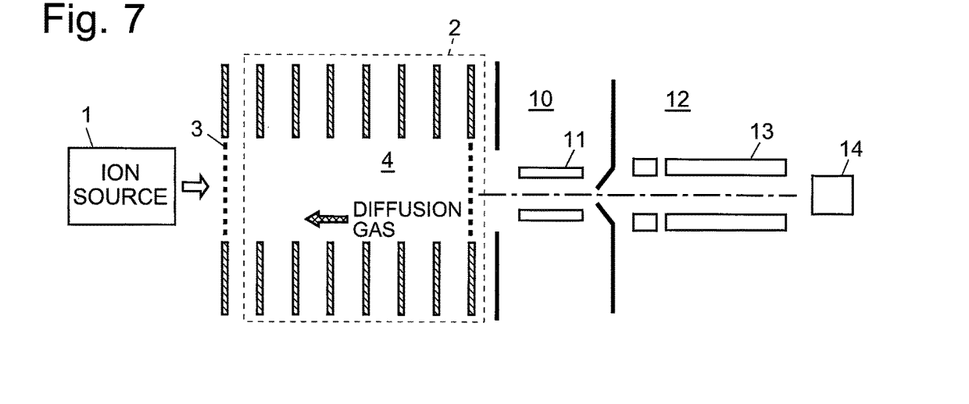
FIG. 7 is a schematic configuration diagram of one embodiment of the mass spectrometer using the ion mobility analyzer according to the present invention.

The previously described ion mobility analyzer can be used as an independent analyzer. However, by incorporating it in a mass spectrometer, an even more useful analyzer can be constructed. FIG. 7 is a schematic configuration diagram of one embodiment of the mass spectrometer using the previously described ion mobility analyzer (IMS-MS system).

In the present example, the ions which have been separated according to their ion mobilities in the drift region 4 are introduced into an intermediate vacuum chamber 10 provided for the differential pumping. The ions are focused by an ion guide 11 placed in the intermediate vacuum chamber 10, to be sent into an analysis chamber 12 maintained at a high degree of vacuum. A quadrupole mass filter 13 and a detector 14 are placed within the analysis chamber 12, whereby the ions which have been separated according to their ion mobilities are further separated according to their mass-to-charge ratios and ultimately detected by the detector 14.

For example, ions derived from compounds A and B having the same elemental composition and the same mass-to-charge ratio but different three-dimensional structures will have different ion mobilities. If the ions which have been almost simultaneously produced from such compounds A and B in the ion source 1 are introduced into the drift region 4 and made to fly, the drift time of the ion derived from compound A will be different from that of the ion derived from compound B due to the difference in their ion mobilities. Consequently, the ion derived from compound A and the ion derived from compound B enter the quadrupole mass filter 13 with a certain interval of time. If the voltage applied to the quadrupole mass filter 13 is set so as to allow those ions to pass through, both kinds of ions derived from compounds A and B pass through the quadrupole mass filter 13 and reach the detector 14, whereas the ions having other mass-to-charge ratios are removed without passing through the quadrupole mass filter 13. The two ions respectively derived from compounds A and B arrive at the detector 14 with a certain interval of time. Therefore, when a chromatogram is created, the peak corresponding to the ion derived from compound A and the peak corresponding to the ion derived from compound B appear at different points in time. From the area value or other properties of each peak, the quantity of each compound A or B can be determined.

In place of the quadrupole mass filter, other types of mass separators, e.g. a time-of-flight mass spectrometer, may be used for the mass separation. A liquid chromatograph may be connected in the previous stage of the previously described mass spectrometer to construct an LC-IMS-MS system. Similarly, a gas chromatograph may be connected in the previous stage of the previously described mass spectrometer to construct a GC-IMS-MS system.

It is also possible to add an ion dissociation unit for dissociating ions in a collision cell or ion trap. For example, the ions which have been separated according to their ion mobilities may be introduced into the collision cell and thereby dissociated, and the product ions produced by the dissociation may be subjected to the mass spectrometry. With this system. $MS^2$ spectra can be obtained for a plurality of compounds which, as described earlier, have the same mass-to-charge ratio yet different ion mobilities. Such information is useful for the structural analysis of those compounds. It is also possible to introduce the product ions produced by dissociation in the collision cell or ion trap into the drift region to measure their ion mobilities or to perform a mass spectrometry for the product ions after separating them according to their ion mobilities. It is also possible to separate ions according to their ion mobilities and then introduce them into a Q-TOF system.

As just described, the previous embodiment is a mere example of the present invention. Any change, modification or addition appropriately made within the spirit of the present invention, not limited to the previously described embodiment or variations, will naturally fall within the scope of claims of the present application.

REFERENCE SIGNS LIST

1 . . . Ion Source
2 . . . Drift Electrode Group
2a . . . Electrode
3 . . . Shutter Gate
4 . . . Drift Region
5, 14 . . . Detector
6 . . . Shutter Voltage Generator
7 . . . Drift Voltage Generator
8 . . . Control Unit
81 . . . Measurement Mode Switcher
9 . . . Input Unit
10 . . . Intermediate Vacuum Chamber
11 . . . Ion Guide
12 . . . Analysis Chamber
13 . . . Quadrupole Mass Filter

The invention claimed is:

1. An ion mobility analyzer for separating ions according to their ion mobilities by introducing the ions in a packet-like form into a drift region and making the ions fly in the drift region, the ion mobility analyzer comprising:
   a plurality of annular or cylindrical electrodes arrayed along an ion beam axis for creating an accelerating electric field within the drift region;
   a voltage supplier for applying voltages to the plurality of electrodes, respectively, with the voltages determined so that an electric field in which a downward gradient of a potential distribution on a central axis of the plurality of electrodes gradually becomes gentler in a moving direction of the ions is created at least within a portion of the accelerating electric field; and
   a controller for controlling the voltage supplier in such a manner that the voltages respectively applied to the plurality of electrodes are changed so as to regulate an effect of compressing the ions into a smaller space in an accelerating direction within the accelerating electric field; wherein:
   a measurement mode is switchable between a high-resolution measurement mode for giving priority to a resolving power and a high-sensitivity measurement mode for giving priority to sensitivity, and the controller sets the voltages applied to the plurality of electrodes, respectively, so that the electric field in which the downward gradient of the potential distribution on the central axis of the plurality of electrodes gradually becomes gentler in the moving direction of the ions is created in at least a portion of the accelerating electric field when the high-resolution measurement mode is specified, while the controller sets the voltages applied to the plurality of electrodes, respectively, so that an electric field in which the potential distribution has a uniform potential gradient is created when the high-sensitivity measurement mode is specified.

2. A mass spectrometer using an ion mobility analyzer for separating ions according to their ion mobilities by introducing the ions in a packet-like form into a drift region and making the ions fly in the drift region, wherein:
   the ion mobility analyzer comprises:
   a) a plurality of annular or cylindrical electrodes arrayed along an ion beam axis for creating an accelerating electric field within the drift region; and
   b) a voltage supplier for applying voltages to the plurality of electrodes, respectively, with the voltages determined so that an electric field in which a downward gradient of a potential distribution on a central axis of the plurality of electrodes gradually becomes gentler in a moving direction of the ions is created at least within a portion of the accelerating electric field; and
   the ion mobility analyzer is placed between an ion source for producing ions originating from a sample and a mass separator for separating ions according to their mass-to-charge ratios, and the ions separated according to their ion mobilities in the ion mobility analyzer are further separated by the mass separator before being detected; wherein:
   the ion mobility analyzer further comprises a controller for controlling the voltage supplier in such a manner that the voltages respectively applied to the plurality of electrodes are changed so as to regulate an effect of compressing the ions into a smaller space in an accelerating direction within the accelerating electric field; and a measurement mode of the ion mobility analyzer is switchable between a high-resolution measurement mode for giving priority to a resolving power and a high-sensitivity measurement mode for giving priority to sensitivity, and the controller sets the voltages applied to the plurality of electrodes, respectively, so that the electric field in which the downward gradient of the potential distribution on the central axis of the plurality of electrodes gradually becomes gentler in the moving direction of the ions is created in at least a portion of the accelerating electric field when the high-resolution measurement mode is specified, while the controller sets the voltages applied to the plurality of electrodes, respectively, so that an electric field in which the potential distribution has a uniform potential gradient is created when the high-sensitivity measurement mode is specified.

\* \* \* \* \*